United States Patent
Leuer et al.

(10) Patent No.: US 8,364,256 B2
(45) Date of Patent: Jan. 29, 2013

(54) METHOD AND APPARATUS OF REMOVAL OF INTRAVASCULAR BLOCKAGES

(75) Inventors: Dennis Leuer, San Francisco, CA (US); Robert Siegel, Beverly Hills, CA (US)

(73) Assignee: Coraje, Inc., San Francisco, CA (US)

( * ) Notice: Subject to any disclaimer, the term of this patent is extended or adjusted under 35 U.S.C. 154(b) by 2564 days.

(21) Appl. No.: 11/273,095

(22) Filed: Nov. 14, 2005

(65) Prior Publication Data

US 2006/0106425 A1 May 18, 2006

Related U.S. Application Data

(60) Provisional application No. 60/628,192, filed on Nov. 15, 2004.

(51) Int. Cl.
*A61N 1/30* (2006.01)
*A61B 17/20* (2006.01)

(52) U.S. Cl. ............... 604/20; 604/21; 604/22; 604/28; 604/500; 606/127; 601/2

(58) Field of Classification Search ............ 604/19–22, 604/27–28, 49, 500, 507–508; 606/127–128; 601/2–3
See application file for complete search history.

(56) References Cited

U.S. PATENT DOCUMENTS

| | | | |
|---|---|---|---|
| 4,586,512 A | 5/1986 | Do-Huu | |
| 4,620,546 A | 11/1986 | Aida | |
| 4,622,952 A | 11/1986 | Gordon | |
| 4,658,828 A | 4/1987 | Dory | |
| 4,718,433 A | 1/1988 | Feinstein | |
| 4,900,540 A | 2/1990 | Ryan et al. | |
| 5,149,319 A | 9/1992 | Unger | |
| 5,196,183 A | 3/1993 | Yudelson | |
| 5,197,946 A | 3/1993 | Tachibana | |
| 5,215,680 A | 6/1993 | D'Arrigo | |
| 5,230,882 A | 7/1993 | Unger | |
| 5,352,435 A | 10/1994 | Unger | |
| 5,380,411 A | 1/1995 | Schlief | |
| 5,399,158 A | 3/1995 | Lauer | |
| 5,405,318 A | 4/1995 | Nita | |
| 5,474,531 A * | 12/1995 | Carter | 604/22 |
| 5,487,390 A | 1/1996 | Cohen | |
| 5,509,896 A | 4/1996 | Carter | |
| 5,695,460 A | 12/1997 | Siegel et al. | |
| 6,635,017 B1 | 10/2003 | Moehring et al. | |
| 6,738,661 B1 * | 5/2004 | Nyhart, Jr. | 604/20 |
| 2003/0032942 A1 * | 2/2003 | Theeuwes et al. | 604/537 |

* cited by examiner

*Primary Examiner* — Quynh-Nhu H Vu
(74) *Attorney, Agent, or Firm* — Walter A. Hackler; Marc G. Martino

(57) ABSTRACT

A method and apparatus for the treatment of intravascular blockages includes introducing a medicament and ultrasound to the blockage, monitoring the blockage or bleeding to determine a status thereof and controlling the agent introduced to the blockage based upon the monitoring.

11 Claims, 1 Drawing Sheet

METHOD AND APPARATUS OF REMOVAL OF INTRAVASCULAR BLOCKAGES

The present application is a continuation of U.S. Ser. No. 60/628,192 filed Nov. 15, 2004, which is to be incorporated herewith in its entirety.

The present invention is generally related to the use of agents to treat (i.e., reduce or remove) intravascular blockages and is more particularly directed to the use of ultrasound imaging in order to control agent dosing.

It is known that ultrasound imaging can be used to locate intravascular thrombi and cranial or subdermal bleeding and it has been further demonstrated that the utilization of ultrasonic waves can improve the diffusion and penetration of medicinal fluids or the like into the vascular system.

Prior art techniques have utilized ultrasonic waves and a catheter wire for diffusion and penetration of medicinal fluids. In this arrangement the ultrasonic oscillating element is connected to the catheter wire outside the body and far from a radiating end of the catheter wire.

The present invention is directed to the discovery that ultrasound diagnostics provide a safe and effective method for dissolving arterial thrombi without excess use of medicaments. That is, the concept of the present invention is directed to introducing an agent to a thrombus, applying the ultrasound to the site or area of the clot to enhance effectiveness, while monitoring, and stopping agent introduction once monitoring shows that the agent has been effective or undesired bleeding occurs. The ultrasound may be transcutaneously applied, applied by means of a transmission wire or generated intravascularly by means of a miniature ultrasonic tool.

SUMMARY OF THE INVENTION

A method for the removal of intravascular blockages in accordance with the present invention generally includes introducing an agent to the blockage, monitoring the blockage size along with cranial or other subdermal bleeding to determine a status thereof and controlling the agent introduced base upon such monitoring. More particularly, the method in accordance with the present invention may also include applying ultrasound to the blockage for enhancement of blockage dissolution.

The step of controlling the agent introduction also encompasses stopping of the agent introduction. Further, the agent introduction control may be based upon removal or reduction of the blockage or subdermal bleeding. In addition, the agent introduction control may include the changing of the agent or modifying the concentration of the agent.

BRIEF DESCRIPTION OF THE DRAWINGS

The advantages and features of the present invention will be better understood by the following description when considered in conjunction with the accompanying drawings in which.

DETAILED DESCRIPTION

Figure 1:
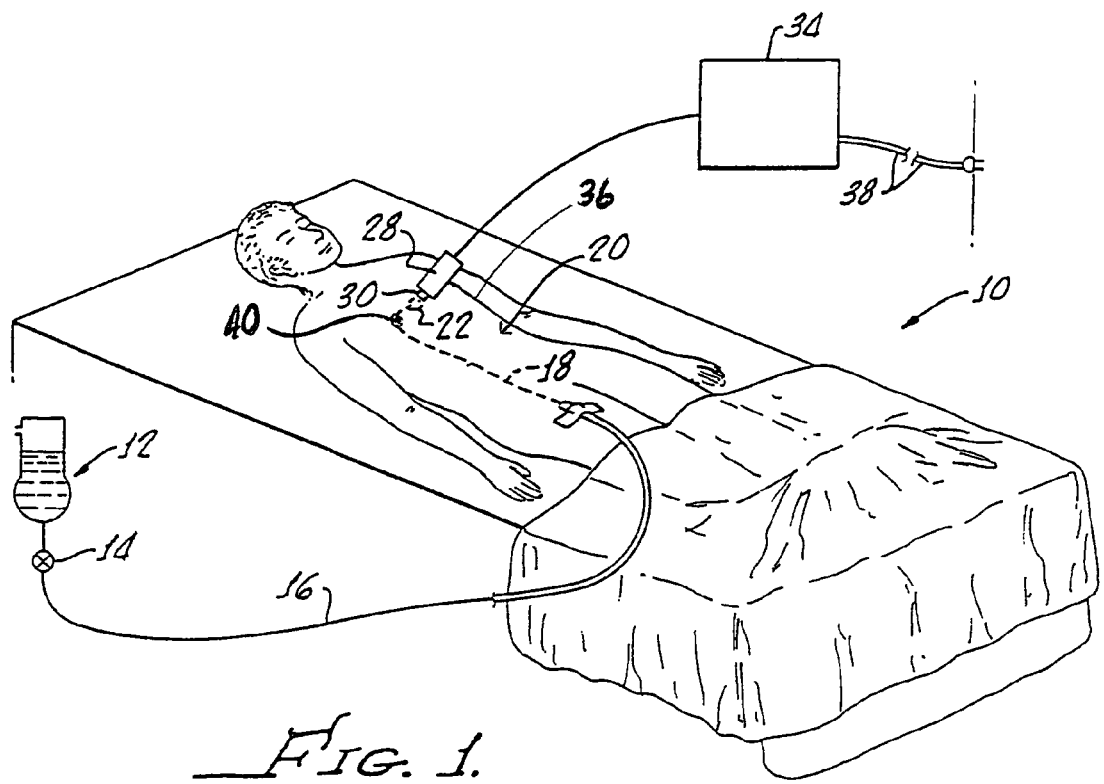
FIG. 1 is a diagram of ultrasonic surgical apparatus in accordance with the present invention method for removing a thrombosis, or blockage, including monitoring of the thrombosis.
Figure 2:
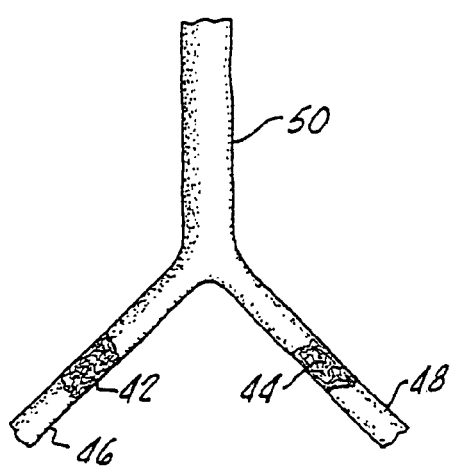
FIG. 2 is a representation of an aorta having bilateral thrombosis induced in iliofemoral arteries.
Figure 3:
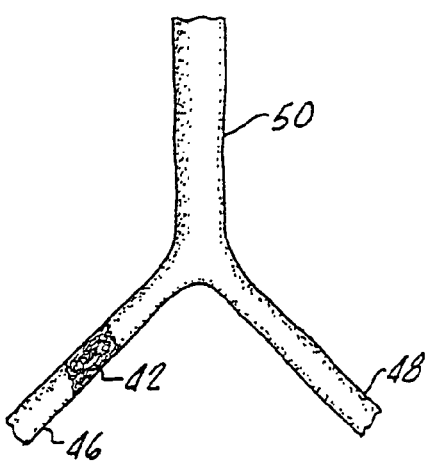
FIG. 3 is a representation similar to that shown in FIG. 2 after one of the thrombi in the iliofemoral arteries has been removed in accordance with the apparatus and method of the present invention.

Turning now to FIG. 1, there is shown apparatus 10 in accordance with the present invention for removal of thrombosis with minimal use of an agent from a vial 12, by way of a valve 14 and a catheter 16. The catheter 16 provides a means for injecting, introducing, and delivering the agents to a vessel 18 within a body 20, proximate a thrombosis 22 illustrated by the dashed lines in FIG. 1.

Alternatively, the agents can be introduced or injected into the vessel 18 proximate the thrombosis 22 in any conventional manner, including, for example, hypodermic needle or the like (not shown).

Selection of the agent based on bleeding or blockage monitoring is of utmost importance. All of the agents herein discussed are considered part of the invention.

Selection among an echo contrast agent such as sonicated albumin, perfluorocarbon, a lysing or thrombolytic agent such as streptokinase or tPA, an anticoagulant such as heparin, antiplatelet agents, such as platelet receptor, like a GP IIb-IIIa inhibitor, such as blockers, Aggrastat (tetrofiban hydrochloride), Integrillin (eptifibatide) a GP IIb-IIIa platelet inhibitor, Reopro (abciximab), a hyperalimentation agent such as intravenous fat emulsions, intralipid and liposyn, or another alternative agent such as Hetastarch or other artificial colloidal solutions, such as Pentaspan®, may be as follows.

If there is no indicated bleeding, or no significant risk of bleeding, a thrombolytic agent may be selected. If there is possible indicated or risk of bleeding, a GP IIb-IIIa inhibitor may be selected. If there is an absolute contraindication due to risk of bleeding, a microbubble, Hetastarch or Pentaspan is preferably selected.

Other indications may be utilized for agent selection.

It should also be appreciated that a combination of agents may be utilized, for example, an echocontrast agent may be used in combination with a thrombolytic agent. For example, an echocontrast agent may be perfluorocarbon, such as, for example, the dodecafluropentane colloid dispersion. The echocontrast agent may be a microbubble medium such as free gas bubbles, stabilized gas bubbles, colloidal suspensions, emulsions and aqueous solutions other than dodecafluropentane. A thrombolytic agent may be any agent having suitable activity such as, for example, streptokinase, staphlokinase, urokinase or a tissue plasminogen activator (tPA). These agents are set forth herein only by way of example and it should be appreciated that, as hereinabove recited, any thrombolytic agent has possible use in accordance with the present invention.

As hereinabove noted, a Hetastarch such as HESPAN®, which is a plasma volume expander, has been found to be effective when used in combination with ultrasound for the lysing of vascular occlusions.

Hetastarch is an artificial colloid derived from a waxy starch composed almost entirely of amylopectin. Hydroxyethyl ether groups are introduced into the glucose units of the starch and the resultant material is hydrolyzed to yield a product with a molecular weight suitable for use as a plasma volume expander and erythrocyte sedimenting agent.

As also hereinabove noted, a colloid suspension or pentastarch, such as Pentaspan®. Pentaspan® or Pentastarch is an artificial colloid derived from a waxy starch composed almost entirely of amylopectin. Hydroxyethyl ether groups are introduced into the glucose units of the starch and the resultant material is hydrolyzed to yield a product with a molecular weight suitable for use in an erythrocyte sedimenting agent.

Additionally, the radiation by ultrasound may include continuous or pulse radiation, still more particularly by way of example only, the amount of active agent introduced may be in concentration less than about 2000 microliters.

The combination of ultrasound has the unique effect of accelerating the onset of lysing activity of a GP IIb-IIIa antiplatelet inhibitor such as Reopro or a GP IIb-IIIa blocker such as, for example, Aggrastat and Integrillin.

Also shown in FIG. 1, is a transducer 28 having a tip 30 positioned exterior to the body 12 and interconnected to an oscillator/driver 34 which provides means for radiating the cardiovascular blockage 22 with ultrasound in order to effect removal thereof. In this embodiment of the present invention, the ultrasound is transmitted transcutaneously and thus the step of radiating ultrasound is a "non-invasive" procedure.

The ultrasonic transducer 28 may be of any conventional design with a suitable frequency range.

The tip 30 provides means for coupling the ultrasound through a body surface 36, thus enabling transcutaneous, or transdermal, application of the ultrasound. It should be appreciated that the tip 30 can include means for focusing the ultrasound as may be required in order to concentrate or specifically direct the ultrasound to a desired area or volume.

The driver 34 is powered through a conventional 110 volt line 38 and may have a power output of up to, for example, about 50 watts through a tip active area of about 0.75 inches by 0.75 inches. The driver 34 and transducer may be operated at a duty cycle 100%, i.e., continuous output, or pulse-operated at, for example, a 50% duty cycle.

Alternately, ultrasound may be transmitted intravascularly, rather than transcutaneously, as hereinabove described. For example, a miniature ultrasonic transducer 40, such as the device described in U.S. Pat. No. 5,269,291, incorporated herein by reference, may be utilized as a means for transmitting ultrasonic energy directly into and proximate the thrombosis 22 and surrounding vascular fluid. The miniature ultrasonic transducer 40 may be inserted into the vessel 18 by means of catheter 16. The transducer 40 may also be utilized for ultrasound imaging.

It should be appreciated that ultrasound may be generated from driver 34 and transmitted therefrom via a guide wire (not shown) directly into the vessel 18, as is well known in the art.

In accordance with one embodiment of the present invention, the apparatus 10 is useful in the method of the present invention, for treating (i.e. reducing or removing) a thrombosis, in which a selected dose of an agent is introduced proximate the thrombosis 22 disposed within a vessel 18 in the body 20. The thrombosis 22 is radiated with ultrasound generated exterior to the body 20, or intravascularly, as described above, to effect treatment or removal of the thrombosis 22. The thrombosis may be monitored for blockage by ultrasound imaging and the dose of thrombolytic agent adjusted to prevent overdosing of the thrombolytic agent. Such overdosing or use being an amount unnecessary after the thrombosis is reduced or removed. Alternative, cranial, or subdermal bleeding may be monitored and the agent controlled in response thereto.

While ultrasound imaging has been herein described as a method for monitoring the blockage or bleeding, it should be appreciated that in accordance with the present invention any type of monitoring methodology may be utilized to determine the extent of the blockage, such as, for example, well known MRI and angiography methods. Ultrasound application and imaging may be done with single or multiple probes also well known in the art.

Prior art administration of the active agent such as, for example, tPA have utilized a drip injection method with a predetermined standard dose (possibly weight adjusted) for 60-90 minutes. As is well known, a significant problem with the use of tPA is bleeding, and this risk is considered to increase with the strength and duration of the dosage. A goal of the present invention is to obtain optimal recanalization without bleeding.

Thus, the present invention is important in reducing the amount of agent utilized in order to prevent overdosing, and undesired effects such as, for example, bleeding, as hereinabove noted. It should also be appreciated that in accordance with the present invention any suitable agents such as, for example, hereinabove set forth. In fact, various agents may be used in combination depending upon the monitored status of the blockage.

Other control over the thrombolytic agent introduction may be affected by changing the concentration of the thrombolytic agent in response to monitoring of the blockage status.

Although there has been hereinabove described a specific method of treating or removal of intravascular blockages in accordance with the present invention for the purpose of illustrating the manner in which the invention may be used to advantage, it should be appreciated that the invention is not limited thereto. That is, the present invention may suitably comprise, consist of, or consist essentially of the recited elements. Further, the invention illustratively disclosed herein suitably may be practiced in the absence of any element which is not specifically disclosed herein. Accordingly, any and all modifications, variations or equivalent arrangements which may occur to those skilled in the art, should be considered to be within the scope of the present invention as defined in the appended claims.

What is claimed is:

1. A method for treating an intravascular blockage, said method comprising:
    applying ultrasound to the blockage;
    introducing an agent to the blockage;
    monitoring the blockage to determine a status thereof; and
    controlling the agent introduced while blockage monitoring.

2. The method according to claim 1 wherein the step of controlling the agent introduction includes stopping agent introduction.

3. The method according to claim 1 wherein the agent introduction control is based upon the blockage monitoring determining removal of the blockage.

4. The method according to claim 1 wherein the agent introduction control includes changing the agent.

5. The method according to claim 1 wherein controlling agent introduction includes changing a concentration of the agent.

6. The method according to claim 1 wherein the ultrasound is applied intravascularly.

7. The method according to claim 1 wherein the ultrasound is applied transcutaneously.

8. The method according to claim 1 wherein the monitoring is done with ultrasound.

9. The method according to claim 8 wherein monitoring and application of ultrasound is done with a single probe.

10. The method according to claim 8 wherein monitoring and application of ultrasound are done with separate probes.

11. The method according to claim 1 wherein the monitoring is done with MRI.

* * * * *